United States Patent [19]
Lindecrantz

[11] Patent Number: 5,139,027
[45] Date of Patent: Aug. 18, 1992

[54] METHOD OF FILTERING AN ANALOG ECG SIGNAL

[75] Inventor: Kaj Lindecrantz, Västra Frölunda, Sweden

[73] Assignee: Cinventa Aktiebolag, Sweden

[21] Appl. No.: 621,518

[22] Filed: Dec. 3, 1990

[51] Int. Cl.⁵ .......................................... A61B 5/0402
[52] U.S. Cl. .............................. 128/696; 364/413.06; 128/704
[58] Field of Search .............. 128/696, 702, 703, 704, 128/705, 708; 364/413.06

[56] References Cited
U.S. PATENT DOCUMENTS

| | | | |
|---|---|---|---|
| 3,654,916 | 4/1972 | Neilson | 128/702 |
| 4,170,992 | 10/1979 | Dillman | 128/702 |
| 4,732,158 | 3/1988 | Sadeh | 128/702 |
| 4,893,632 | 1/1990 | Armington | 128/696 |

OTHER PUBLICATIONS

K. G. Lindecrantz & H. Lilja; New Software QRS Detector Algorithm Suitable for Real Time Applications with Low Signal-to-Noise Ratios; J. Biomed. Eng. 1988, vol. 10, May, 1988, pp. 280-284.

K. G. Lindecrantz; A Microprocessor-Based System for Averaging Abdominal & Direct Fetal ECG, 1983, Tech. Report 2:83 Research Lab. of Med. Elec., Chalmers U. of Tech.

*Primary Examiner*—William E. Kamm
*Assistant Examiner*—Kennedy J. Schaetzle
*Attorney, Agent, or Firm*—Marshall & Melhorn

[57] ABSTRACT

In a method of filtering an analog ECG signal, ECG complexes are located by means of a template which is evaluated and given a quality mark depending on how well it performs its function of achieving a correct heart rate value and triggering of the ECG complexes.

4 Claims, 5 Drawing Sheets

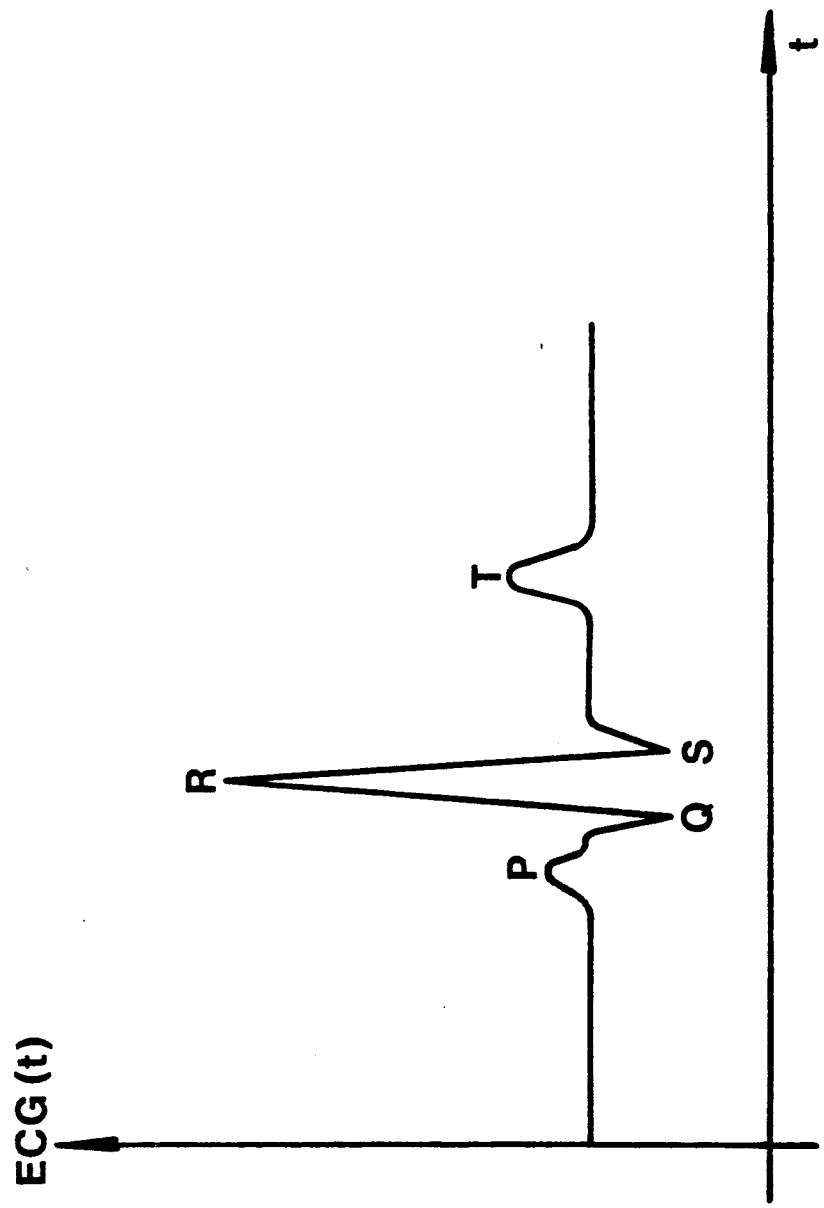

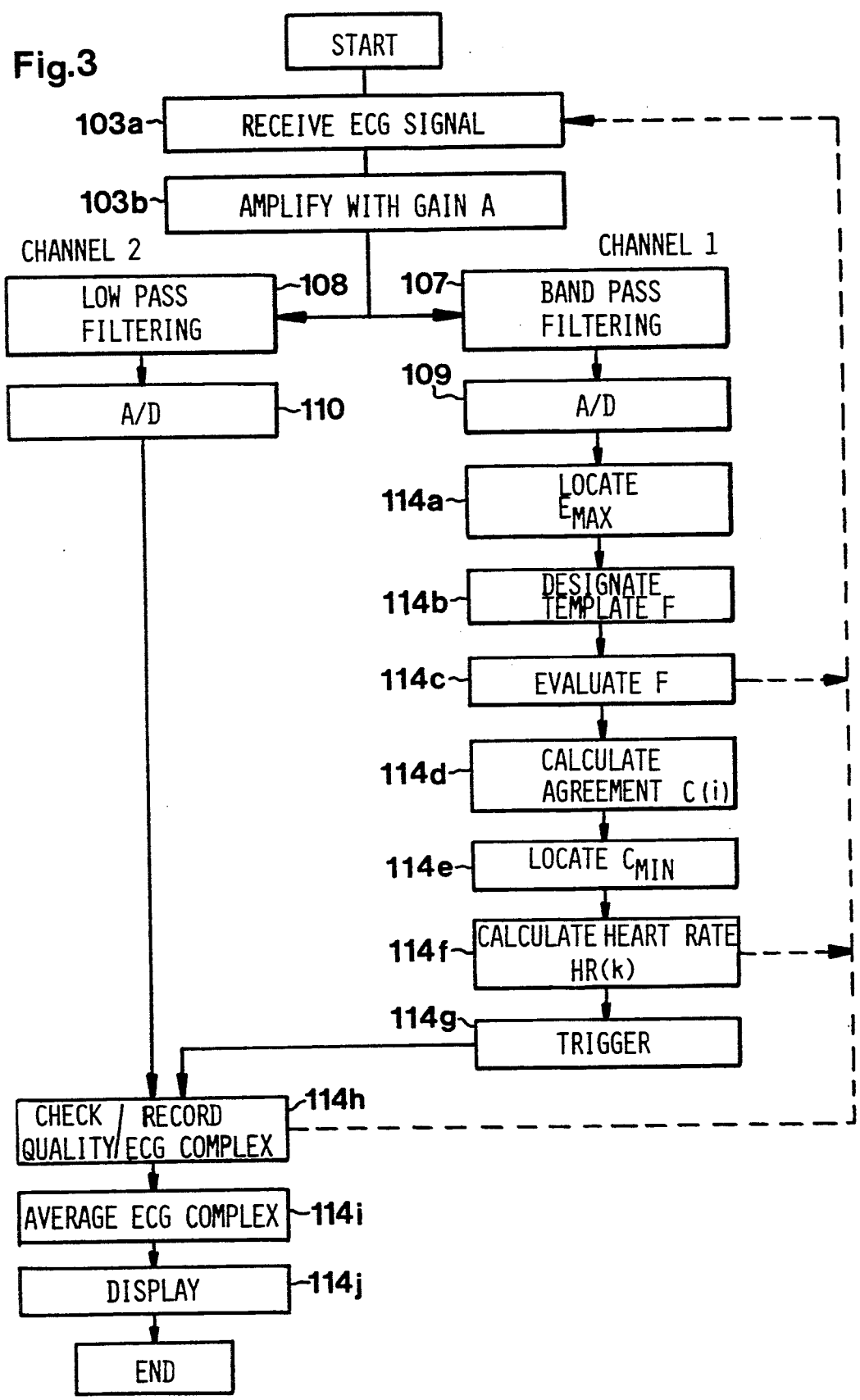

METHOD OF FILTERING AN ANALOG ECG SIGNAL

BACKGROUND OF THE INVENTION

The present invention relates to a method of filtering an analog ECG signal.

The heart function of a patient is normally monitored by means of electrodes emitting an electric, analog ECG signal reflecting the electrical activity of the heart.

The technical field of the invention generally encompasses the processing of analog ECG signals. This signal processing comprises receiving, preparing and evaluating a recorded ECG signal and its characteristic components.

An ECG signal contains certain characteristic signal components manifesting themselves in specific waves designated P, Q, R, S and T. These components constitute an ECG complex.

In an ideal ECG signal, the ECG complexes appear distinctly. In practice, the ECG signal however exhibits both systematic and random errors, making it more difficult to locate the ECG complexes. Thus, the ECG signal is affected by interference, e.g. interference pulses or noise, which is superimposed on the signal.

SUMMARY OF THE INVENTION

It is difficult to analyse an ECG signal because of the above-mentioned errors. A particular problem lies in analysing the individual components of the ECG signal in real time. Also, it is difficult to make a real time analysis with simple electronic equipment.

The object of the present invention is to provide a filtering method solving the above-mentioned problems and complying with the requirements specified below.

The invention should permit filtering the ECG signal to filter off irrelevant, interfering information. The invention should permit preparing the ECG signal for subsequent computer-aided analysis. Further, the invention should permit locating ECG complexes.

According to the invention, these objects are achieved by means of a method having the features stated in the accompanying claims.

BRIEF DESCRIPTION OF THE DRAWINGS

The invention will be described in more detail hereinbelow with reference to the accompanying drawings, in which:

FIG. 2 shows an ECG signal,

FIG. 3 is a flow chart according to the invention, and

DESCRIPTION OF THE PREFERRED EMBODIMENT

Figure 1:
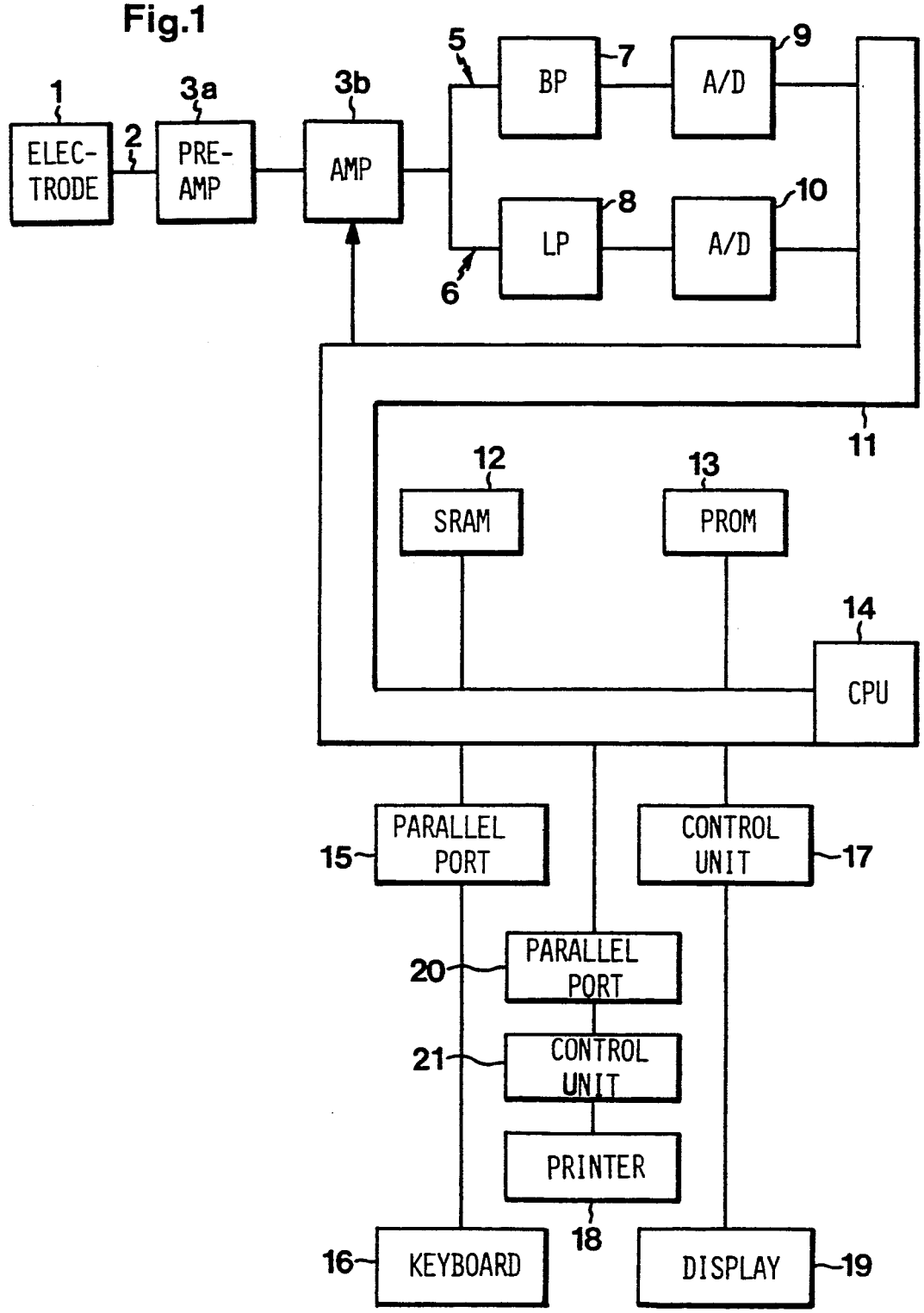
FIG. 1 illustrates an arrangement for implementing the method of the invention.

FIG. 1 shows the preferred embodiment of the invention. An electrode 1 is connected by an electrode input terminal 2 to a preamplifier 3a amplifying the signal to a suitable operating level. The preamplifier 3a is connected to an amplifier 3b. From the amplifier 3b pass a first channel 5 and a second channel 6. The first channel 5 has a band-pass filter 7, while the second channel 6 has a low-pass filter 8. A first analog-to-digital converter, A/D converter 9, is connected in cascade with the band-pass filter 7. A second analog-to-digital converter, A/D converter 10, is connected in cascade with the low-pass filter 8. The first and second A/D converters are connected to a data bus 11.

A static random access memory SRAM 12 and a programmable read-only memory PROM 13, two parallel ports 15, 20, and a control unit 17 are each connected to the data bus 11. Further, a central processing unit CPU 14 is connected to the data bus. A keyboard 16 is connected to the first parallel port 15. The control unit 17 is connected to a display 19, and the second parallel port 20 is connected via a control unit 21 to a printer 18.

A functional description of the preferred embodiment of the present invention will now be given.

To be able to fully understand the function, we must first know the signal being processed. FIG. 2 shows an ideal ECG signal, with the characteristic waves. From left to right, they are designated P, Q, R, S and T. Usually, one speaks about the heart rate HR. The inverse of HR is the time HT between two heart beats, which also corresponds to the distance between two R waves.

Via the electrode 1, a recorded ECG signal is supplied to the preamplifier 3a amplifying the signal 1100 times. After the preamplification, the signal passes on to the amplifier 3b where it is amplified by a gain factor A which is automatically adjustable according to the invention, as described below.

After amplification, the ECG signal enters both the first channel 5 and the second channel 6. The band-pass filter 7 preferably allows signals of 5–60 Hz to pass through, while the low-pass filter 8 allows signals below 100 Hz to pass through. After filtering, the signals are digitized in the respective channel by means of the A/D converters 9 and 10.

The central processing unit CPU 14, preferably being an "8085 processor" having a frequency of 5 MHz, processes the digitized ECG signals arriving via the data bus in the central processing unit CPU 14. The central processing unit then uses a program which is stored in the programmable read-only memory PROM 13. The static random access memory SRAM 12 serves as working storage for the CPU and is used, inter alia, for storing part results during ongoing calculations.

By means of a keyboard 16, the central processing unit is operated, e.g. for printing out the result of an ECG signal filtering operation.

Reference is now made to FIG. 3 where the blocks corresponding to components in FIG. 1 have the same reference numerals, but increased by 100.

Figure 4A:
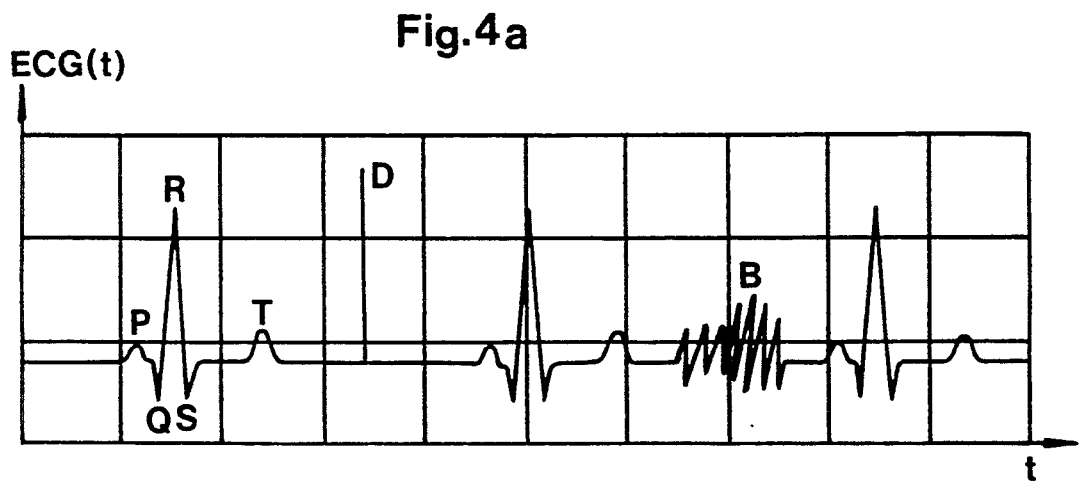
FIGS. 4a–e show the graphs of the curves pertaining to FIG. 3.
Figure 4B:
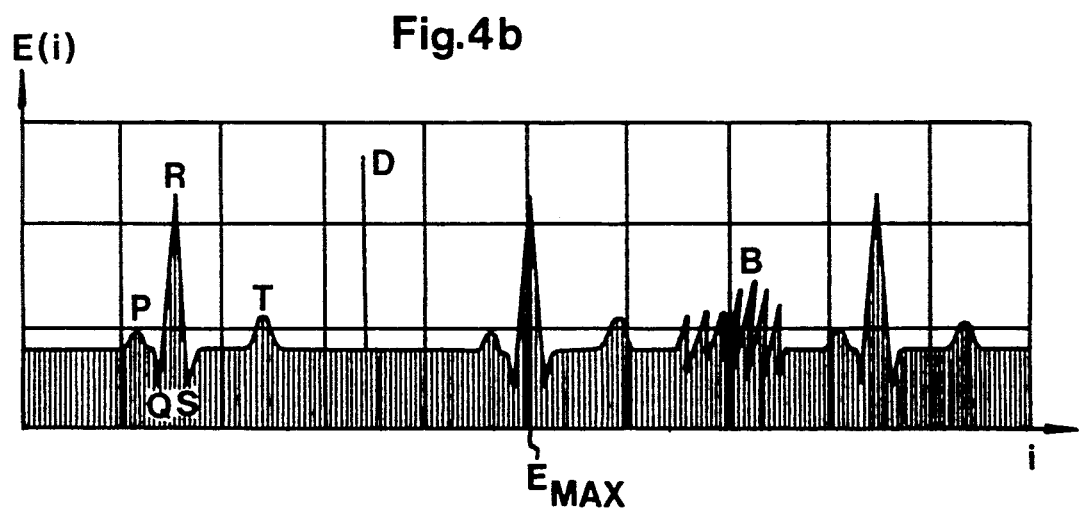
Figure 4C:
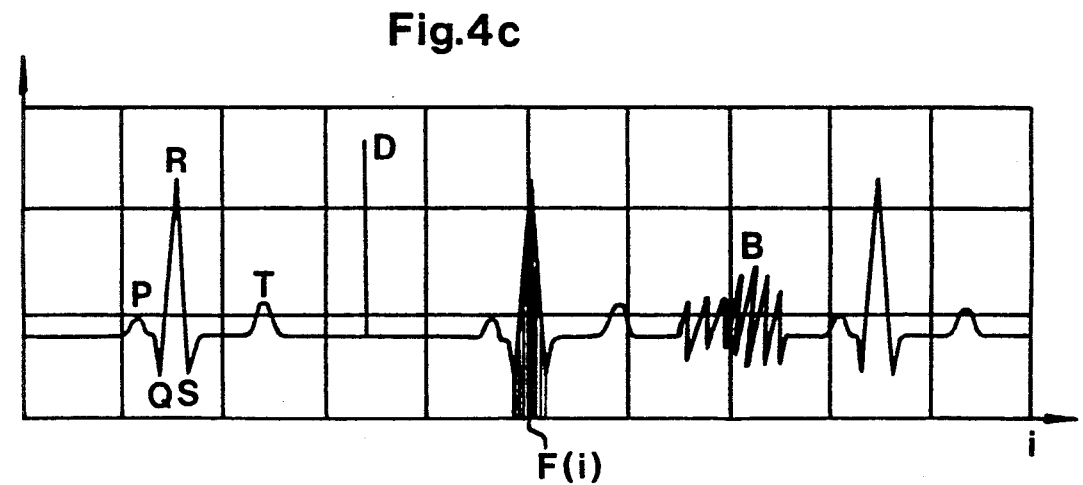

A recorded analog ECG signal is received in a stage 103a. This ECG signal seldom is as unaffected as the signal shown in FIG. 2. FIG. 4 shows more realistic ECG signals. For the sake of clarity, FIG. 4 shows an ECG signal exhibiting only two types of interference: a strong interference spike D and a short-duration noise B. FIG. 4a shows the ECG signal amplified by an adjustable gain factor A in a stage 103b.

After the stage 103b, the ECG signal passes, both through a first channel to a stage 107 and through a second channel to a stage 108. In the stage 107, band-pass filtering (5–60 Hz) of the ECG signal is performed before a stage 109 in which the analog ECG signal is digitized to a signal sequence E of digital discrete samples E(1), E(2) ... E(i) .... The sampling frequency is 500 Hz, i.e. the time between two samples is 2 ms, and digitizing is effected with an 8-bit resolution, i.e. 256 levels.

In a stage 114a, a search is effected to locate the maximum value $E_{max}$ in a sequence comprising about 1.5 s, i.e. about 750 discrete samples. Theoretically, the R wave should be a maximum, i.e. the position of $E_{max}$. See FIG. 4b. A strong interference spike, as at D, may in some cases be higher than the R wave and may then be presumed to be the R wave, in which case $E_{max}$ is located at an incorrect position.

The located value $E_{max}$ is the starting point for providing a template F. See FIG. 4c. A number of samples, corresponding to a given space of time before and after $E_{max}$, are copied in a stage 114b and designated as the template F. In all, the template comprises 32 samples with $E_{max}$ in the middle, i.e. a total of 64 ms, such that $F=F(1), F(2) \ldots F(i) \ldots F(32)$.

In a stage 114c, it is evaluated whether the template has a reasonable amplitude. The sampling values of the template are summed up. If the sum (actually the integral across the template) is between two selectable limit values, in this case 20 and 35, the template is accepted. Otherwise, the process returns to stage 103a. At the same time, the gain factor A is adjusted up or down in selectable steps, e.g. 1.5 dB. In this case, the selectable starting value A is amplification twice. From the starting value, the gain factor A can be reduced in a number of steps, e.g. four steps, and increased in a number of steps, e.g. 11 steps in all, i.e. by a total of −6 dB and +16.5 dB, respectively. When the template F is accepted, the process proceeds to a stage 114d where the agreement between the signal sequence E and the template F is calculated according to the following formula $$C(i) = \sum_{n=-4}^{5} |E(i + n) - F(n + 16) - \bar{E}(i) + \bar{F}|$$

wherein $$E(i) = \frac{1}{32} \sum_{n=-15}^{16} E(i + n)$$

$$\bar{F} = \frac{1}{32} \sum_{n=1}^{32} F(n)$$

C being an agreement sequence which is continuously calculated. See FIG. 4d.

Figure 4D:
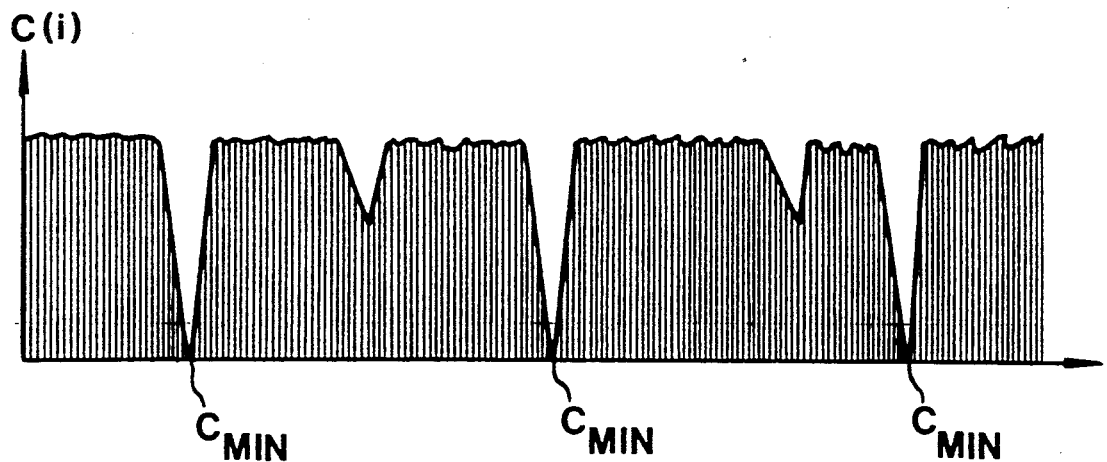
Figure 4E:
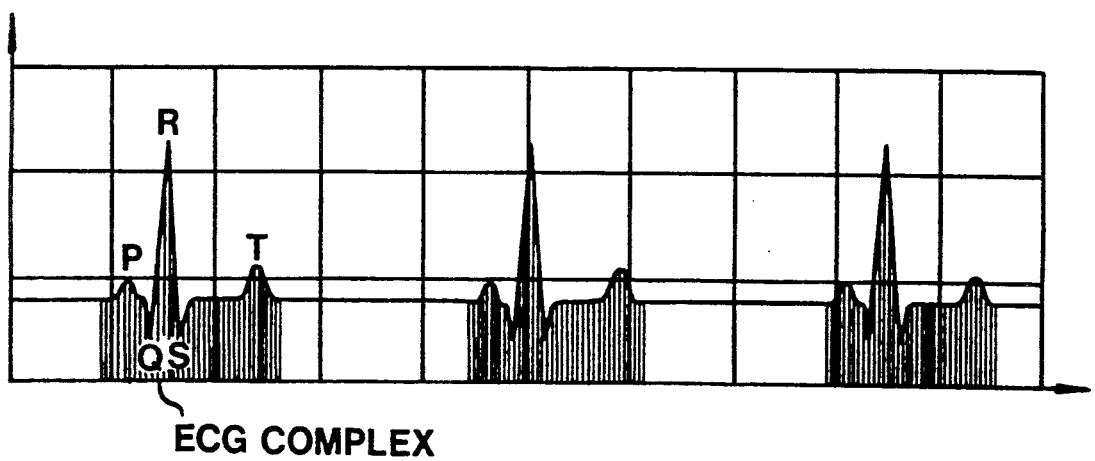

In a stage 114e, the minimum values $C_{min}$, i.e. the positions of optimum agreement between E and F, are located in the agreement sequence C. As used herein, "optimum agreement" means that $C_{min}$ falls below a predetermined value. In FIG. 4d, it is seen that there is a fairly good agreement for interference D and B, whereas optimum agreement for the correct positions of the R waves. If the noise interference B in stage 114c had been accepted as a basis for the template F, the agreement would have been optimal at the position of B while it would have been much poorer for the R wave positions.

In the following stage, it is checked whether each $C_{min}$ is at the correct position, i.e. at a probable R wave position. If this is the case, the template F has been correctly selected and the correct $E_{max}$ has been located in the stage 114a. If, on the other hand, this is not the case, the template F has probably not been correctly selected. The reason for this may be that $E_{max}$ has been incorrectly located, e.g. on an interference spike D.

The template F is therefore evaluated by means of a variable quality mark X. The purpose of this evaluation is to remove an incorrect template as soon as possible to ensure adequate filtering.

It will now be described in more detail how filtering is effected:

In a stage 114f, the located minimum values $C_{min}$ of C are used for calculating the heart rate HR(k) where k is the ordinal number of the heart beat counted from the start of the calculation, and for evaluating the reliability of this calculated heart rate, as will be described below.

Each new heart rate value HR(k) is compared with a test mean value $HR_T(k)$ which is:

$$HR_T(k) = \tfrac{1}{2} HR_T(k-1) + \tfrac{1}{2} HR(k-1).$$

If the absolute value of the difference between HR(k) and $HR_T(k)$ is greater than 28 heart beats per min (i.e. $|HR(k) - HR_T(k)| > 28$), HR(k) is not accepted. HR(k) however contributes to the next test mean value as follows:

$$HR_T(k+1) = \tfrac{1}{2} HR_T(k) + \tfrac{1}{2} HR(k).$$

If the absolute value is however equal to or less than 28, HR(k) is accepted.

In a stage 114g, the positions of the accepted, located minimum values $C_{min}$ are outputted for triggering a quality check and optionally recording ECG complexes in the ECG signal fed through the channel 2.

The ECG signal in the channel 2 has passed through a low-pass filtering stage 108 (all frequencies below 100 Hz are allowed to pass through) and derives from the same analog ECG signal as the signal just processed in channel 1.

In a stage 110, the analog signal in channel 2 is converted into a sequence $E_2$ having a sampling frequency of 500 Hz, i.e. the time between two samples is 2 ms. This digitizing takes place with an 8-bit resolution.

In a stage 114h is effected, as mentioned above, a quality check of the ECG complexes in the ECG signal supplied through the channel 2. The exact procedure of this quality check will be described in more detail hereinbelow. The presumed ECG complexes accepted in the quality check are recorded as actual ECG complexes and are passed on to a stage 114i. The recorded ECG complex comprises 700 samples, and the R wave is slightly offset in one direction, such that 200 samples are located before the R wave. See FIG. 4e. In the stage 114i, 20 ECG complexes are averaged, by addition or superposition. In the next stage 114j, the operator can choose to show the averaged ECG complex either on the display 19 or on the printer 18.

At the stage 114i, the filtering of the analog ECG signal is completed and further processing of the digital signal can easily be carried out.

During filtering, the template F (see FIG. 4c) has been used. The adequacy of the template has been checked by means of the above-mentioned quality mark X. When a template F has been accepted in the stage 114d, the template is initially given a quality mark X=15 points. The number of points may increase or decrease depending on how well the template performs its task, i.e. to achieve a correct heart rate value HR(k) and triggering of the ECG complexes.

If the heart rate value HR(k) is accepted, the template is considered to be satisfactory and one point is added to the quality mark. The template is considered to be inadequate if it produces a rejected heart rate value HR(k)

according to stage 114f, and one point is then subtracted from the quality mark X.

First it must however be checked whether the tested signal is good or bad before a point is subtracted from the quality mark X. See FIG. 4e. If the signal is filled with noise or if it is saturated, i.e. resembles a direct current, the rejected heart rate value is probably not due to the quality of the template but rather to a poor signal. In such a case, no point should be subtracted from the quality mark X, nor added to it, since no accepted heart rate value HR(k) has been achieved.

Every time an ECG complex triggering has been accepted in stage 114f, one point is added to the quality mark X. However, the mark X has a maximum permissible value, about 35 points, since it is desirable that a template which has operated satisfactorily for a long period of time and suddenly starts giving poor results should be discovered immediately. If no triggering is achieved over a long period of time, there is a time-out function making the filtering restart in the stage 103a. If the quality mark in the stage 114f drops to a minimum value, in the instant case equal to 0, the template is rejected and filtering restarts in the stage 103a with a new ECG signal.

If interference, e.g. noise, occurs around the recorded R wave in the ECG complex, this may indicate that the template has been recorded around an $E_{max}$ on e.g. a high T wave instead of an R wave. Yet the heart rate value is correct and so, the quality mark X has not been affected in the previous stage 114f despite the fact that the template F is incorrectly selected. This interference is discovered in that the program in the stage 114h checks a number of samples, e.g. 500, around the presumed R wave in the ECG complex. If noise occurs, the ECG complex is rejected and one point is subtracted from the quality mark X. If there is no interference around the R wave, the ECG complex is accepted and one point is added to the quality mark X. If the quality mark drops to the minimum value, filtering restarts in the stage 103a.

The filtered and digitized ECG signal, which is in the form of averaged ECG complexes and heart rate HR data, is suited for computer-aided processing. For example, the T/QRS ratio is calculated as follows: From the R wave backward stepping is done until the isoelectric level between the P peak and Q wave is obtained. This level is recorded, and forward stepping is thereafter done until the T wave is encountered. The amplitude is compared with the isoelectric level, recorded and divided by the difference between the highest and the lowest point of the QRS complex.

The method according to the invention briefly means that a template is produced, that the template is used for active filtering, that the shape and function of the template is checked during the entire filtering operation and that the template is optionally replaced if its shape or function is bad. The invention is not restricted to the embodiment described above but may be modified in many different ways within the scope of the accompanying claims.

What I claim and desire to secure by Letters Patent is:

1. A method of filtering an analog ECG signal, characterized by the steps of
   i) receiving and monitoring an ECG signal
   ii) providing a template F by:
   a) locating a presumed ECG complex within a predetermined space of time of said ECG signal and determining a maximum value ($E_{max}$) thereof,
   b) copying said ECG signal during a given time interval before and a given time interval after the maximum value $E_{max}$ of said located, presumed ECG complex,
   c) designating said ECG signal, copied during said given time intervals, as said template F, if satisfying predetermined conditions;
   iii) preparing the ECG signal by:
   a) continuously comparing said template F and said ECG signal at each point of time,
   b) locating the position for optimum agreement $C_{min}$ between said template and said ECG signal,
   c) recording said ECG signal during a given time interval before and a given time interval after the position for said optimum agreement $C_{min}$ as an ECG complex, if satisfying predetermined conditions; and
   iv) averaging several recorded ECG complexes.

2. Method as claimed in claim 1, wherein said receiving and monitoring step i) comprises
   a) amplifying the ECG signal by an adjustable gain factor A,
   b) digitizing the amplified ECG signal to a signal sequence E of discrete samples, with a resolution of a given number of bits and at a given sampling frequency,
   wherein said step ii) of providing said template F comprises evaluating the template F by adding up the sample values of said template and comparing them with a given permissible interval, such that said template F is either accepted or rejected, said gain factor A, in case the template is rejected, being adjusted and said filtering recommencing by said reception step, whereas, if accepted, the template F is recorded; and
   wherein said step of providing said template is repeated until a template is recorded.

3. Method as claimed in claim 1, wherein said receiving step i) comprises
   a) amplifying the ECG signal by an adjustable gain factor A,
   b) digitizing the amplified ECG signal with an 8-bit resolution, to a signal sequence E of discrete samples with a sampling interval of 2 ms,
   wherein said step ii) of providing said template F comprises
   b) copying said signal sequence E for 32 ms before and 32 ms after the maximum value $E_{max}$ thereof,
   c) recording the template F if the integrated value thereof, i.e. the sum of the sample values of the template, is within a predetermined range of 20–35, or rejecting the template F and repeating the step of providing the template until a template is recorded.

4. Method as claimed in claim 1, wherein said step ii) of providing said template F comprises
   d) assigning the template F a quality mark X of an initial value;
   wherein said step iii) of preparing said ECG signal comprises
   b₁) calculating in said substep of locating said optimum agreement, the heart rate HR(k) for each located position $C_{min}$,
   b₂) comparing the heart rate HR(k) with a test mean value $HR_T(k)$ based on previous heart rate values, and accepting said heart rate if $|HR(k) - HR_T(k)|$ is less than a given value, said quality mark being incrementally increased upon acceptance and incrementally decreased upon rejection, b₃) comparing said quality mark with a selected maximum permissible quality mark value $X_{max}$ and a selected minimum permissible quality mark value $X_{min}$, and b₄) rejecting said template F if said quality mark X falls below said minimum quality mark value, and repeating said step of providing said template.

* * * * *